(12) United States Patent
Finck et al.

(10) Patent No.: US 11,801,204 B2
(45) Date of Patent: Oct. 31, 2023

(54) NASOGASTRIC DEVICE AND METHOD

(71) Applicants: UNIVERSITY OF CONNECTICUT, Farmington, CT (US); CONNECTICUT CHILDREN'S MEDICAL CENTER, Hartford, CT (US)

(72) Inventors: Christine Finck, South Glastonbury, CT (US); Liisa Kuhn, West Hartford, CT (US); Kelly A. Burke, Grafton, MA (US); Todd Jensen, Burlington, CT (US)

(73) Assignees: CONNECTICUT CHILDREN'S MEDICAL CENTER, Hartford, CT (US); UNIVERSITY OF CONNECTICUT, Farmington, CT (US)

( * ) Notice: Subject to any disclaimer, the term of this patent is extended or adjusted under 35 U.S.C. 154(b) by 646 days.

(21) Appl. No.: 16/979,275

(22) PCT Filed: Mar. 11, 2019

(86) PCT No.: PCT/US2019/021589
§ 371 (c)(1),
(2) Date: Sep. 9, 2020

(87) PCT Pub. No.: WO2019/173819
PCT Pub. Date: Sep. 12, 2019

(65) Prior Publication Data
US 2020/0397666 A1    Dec. 24, 2020

Related U.S. Application Data

(60) Provisional application No. 62/640,796, filed on Mar. 9, 2018.

(51) Int. Cl.
*A61J 15/00* (2006.01)
*A61M 25/10* (2013.01)

(52) U.S. Cl.
CPC ....... *A61J 15/0003* (2013.01); *A61J 15/0049* (2013.01); *A61M 2025/1061* (2013.01)

(58) Field of Classification Search
CPC .... A61J 15/00; A61J 15/0003; A61J 15/0007; A61J 15/0011; A61J 15/0015;
(Continued)

(56) References Cited

U.S. PATENT DOCUMENTS

| 4,100,246 A | 7/1978 | Frisch |
| 4,351,330 A * | 9/1982 | Scarberry ............ A61N 1/0517 607/124 |

(Continued)

FOREIGN PATENT DOCUMENTS

| WO | 9504564 | 2/1995 |
| WO | 2006089811 A1 | 8/2006 |

OTHER PUBLICATIONS

Esophageal Feeding Tube with Balloon Dilator, Mila International Inc., https://www.milainternational.com/products/strictures-tube/esophageal-feeding-tube-with-balloon-dilator-1.html, Jan. 2018, 4 pp.
(Continued)

*Primary Examiner* — Tiffany Legette
(74) *Attorney, Agent, or Firm* — CANTOR COLBURN LLP

(57) ABSTRACT

A nasogastric device and method is provided, including a first flexible tube configured to be threaded through the nose of a patient, down the esophagus and into the stomach for enteral feeding, a second flexible tube disposed adjacent to the first tube having a distal end, the distal end of said second tube configured to terminate inside the esophagus for deliv-
(Continued)

ery of liquids to the esophagus or for sampling of the local environment, an inflatable balloon configured around said first and second flexible tubes, a third flexible tube configured to inflate said inflatable balloon; and a fourth flexible tube communicating with an exterior portion of said inflatable balloon, the fourth tube configured to transport suspensions or solutions of materials; and an elastomeric sleeve which is used to control delivery of therapeutic suspensions of solutions of materials to the exterior of the device to the adjacent esophageal tissue.

19 Claims, 5 Drawing Sheets

(58) Field of Classification Search
CPC ................ A61J 15/0019; A61J 15/0034; A61J 15/0026; A61J 15/0042; A61J 15/0049; A61J 15/0073; A61J 15/0069; A61J 15/0061
See application file for complete search history.

(56) References Cited

U.S. PATENT DOCUMENTS

| | | | |
|---|---|---|---|
| 5,318,530 A * | 6/1994 | Nelson, Jr. .......... | A61J 15/0049 604/528 |
| 2009/0216186 A1 * | 8/2009 | Nath .................. | A61B 17/3415 604/103.05 |

OTHER PUBLICATIONS

International Application No. PCT/US19/21589 International Search Report and Written Opinion dated May 17, 2019, 19 pages.

* cited by examiner

NASOGASTRIC DEVICE AND METHOD

CROSS REFERENCE TO RELATED APPLICATIONS

This is a U.S. National Stage filing of Application No. PCT/US2019/021589, filed on Mar. 11, 2019, which claims the benefit of U.S. Provisional Application No. 62/640,796 filed on Mar. 9, 2018, the disclosures of which are incorporated herein by reference.

FIELD

The present technology is generally related to nasogastric devices for treatment of esophageal narrowing and other esophageal conditions, especially in infants.

BACKGROUND

Numerous medical conditions affecting both adults and children require the replacement or repair of a section of the esophagus. These conditions include esophageal atresia, caustic ingestions, and esophageal carcinomas. Esophageal atresia ("EA") is a rare congenital abnormality where a baby is born with an incomplete esophagus and the inability for food to travel from the mouth to the stomach. It may be estimated that Esophageal atresia occurs in 1 of every 2,500-3,500 live births. Further each year several thousand children worldwide are born with one of the four types of esophageal atresia.

In the United States, an estimated 5,000-15,000 caustic ingestions occur per year. The ingestion of these chemicals can be a devastating injury depending on the amount of esophageal tissue that becomes necrotic. Esophageal carcinoma is the sixth most common cause of cancer death in the world each year. Furthermore the five-year survival rate ranges from 15-20%. In addition to radiation treatment, surgery is typically the most successful treatment for esophageal carcinoma as the cancerous segment is removed.

Current surgical options available for the treatment of EA, esophageal carcinoma or caustic ingestions focus upon either the replacement of the esophageal tissue with other autologous tissue like gastric pull-up or colon interposition, or mechanically stretching the current esophageal tissue to bridge the gap, such as the Foker procedure. The Foker procedure is performed by placing sutures on the small pieces of esophagus that are present and stretching them over a period of time, followed by connection of the two ends. Although this procedure results in the use of esophageal tissue to replace this gap, there are significant complications. These complications include anastomotic leakage and esophageal strictures. Such approach also requires at least two separate surgical interventions, which is costly since the patient will stay in the hospital for several months.

Colon or small intestine can be utilized to bridge the gap; however, since the structure and function of these tissues is not the same as the esophagus, the approach can associate with complications including reflux, strictures or even subsequent replacement of the segment due to significant dilation. A gastric pull-up procedure can also be performed that tubularizes the patient's stomach and brings it up into the patient's thoracic cavity. Complications seen with this type of procedure are similar to that of the other repair options mentioned above.

Anastomotic stricture is a well-recognized postsurgical complication of esophageal surgery and occurs in 18-50% of patients with surgically treated esophageal diseases (see PRIOR ART FIG. 1, which shows diagram of exemplary esophageal narrowing generally at 12). The reoccurrence rate of esophageal strictures has ranged from 35% to 59% of patients. Esophageal strictures are typically treated with endoscopic balloon dilation under sedation.

PRIOR ART FIG. 2 illustrates an endoscope, shown generally at 14, having a distal end 16 that is fed through the mouth of a patient to the area of narrowing, which procedure requires general anesthesia. During the procedure, the endoscope may be used to inject medicine at the site of the stricture.

PRIOR ART FIG. 3 illustrates a balloon dilator, shown generally at 18 that includes a balloon 20 used to dilate a stricture. The dilator 18 fits through endoscope 14 and, under vision, can balloon dilate a stricture. Such a balloon dilator 18 must be removed back through the endoscope subsequent to dilation.

Another method that can be used in conjunction with esophageal dilations is the use of esophageal stents. Referring to PRIOR ART FIG. 4, an exemplary esophageal stent, shown generally at 22, may be deployed with an endoscope across the narrowing. However, the stents themselves can lead to granulation tissue formation and can even cause tissue damage due to migration. Due to the high recurrence rate of esophageal strictures, the number of sedations required for a given patient to have relief of symptoms can also be very high, which carries its own set of side effects.

As we have noted above, when esophageal strictures occur in patients undergoing esophageal surgery, pneumatic dilation is required. This is a procedure that requires anesthesia and is not cured with a single dilation, rather needs repetitive dilations for months. Accordingly, weekly to monthly dilations are performed using an endoscope and pneumatic dilator. In a separate procedure under anesthesia, a gastrostomy feeding tube ("G-Tube") is surgically placed in the stomach and brought out through the abdominal wall to allow for enteral feeding to provide nutrition until the esophagus can be repaired. PRIOR ART FIG. 5 illustrates an exemplary G-Tube, shown generally at 20 and including a feeding port 26, a clamp 28, extension tubing 30 and a feeding syringe 32.

In some refractory cases of esophageal stricture, topical application of medicine such as mitomycin C has been described with some benefit. However, this also requires endoscopy with directed delivery of the medicine.

In severe cases, such as seen in esophageal cancer, esophageal stents are placed which also requires endoscopy and anesthesia. The known common complication from stenting is migration of the stent requiring endoscopic removal and replacement. Drugs are currently delivered orally by swallowing a suspension like steroids, which treats the entire esophagus and is not targeted to the specific site of concern.

New medical devices and methods are needed in the art for esophageal surgery that avoid or reduce complications associated with such surgery, including esophageal strictures.

SUMMARY

The techniques of this disclosure generally relate to devices and methods to reduce invasive interventions for esophageal surgery by provision of a device that removes the need for repetitive, separate pneumatic dilations for esophageal strictures and separate use of gastric invasive installation of a feeding tube. Such a device advantageously provides combined esophageal stenting, pneumatic dilation, drug delivery and enteral feeding aspects.

In one aspect, the present disclosure provides a first flexible tube having a distal end configured to be threaded through the nose of a patient, down the esophagus and into the stomach for enteral feeding, a second flexible tube disposed adjacent to the first tube having a distal end proximate to the distal end of said first flexible tube, the distal end of said second tube configured to terminate inside the esophagus for delivery of liquids to the esophagus or for sampling of the local environment, a first inflatable balloon configured around said first and second flexible tubes, the inflatable balloon disposed proximal to the distal end of the first and second flexible tubes, a third flexible tube in fluid communication with said balloon configured to inflate said inflatable balloon; and a fourth flexible tube having a distal end portion communicating with an exterior portion of said first inflatable balloon, the fourth tube configured to transport suspensions or solutions of materials, such as therapeutic molecules into a space exterior to said first inflatable balloon. It should be recognized that one or more tubes described herein may be placed alongside or inside of other tubes.

In another aspect, the fourth tube communicates with an elastomeric sleeve that is provided exterior to and at least partially around the first inflatable balloon, the elastomeric sleeve configured to receive and dispense therapeutic molecules to esophageal tissue outside the balloons. In further aspects, the elastomeric sleeve includes perforations on a surface thereof; and inflation of the first inflatable balloon forces therapeutic molecules contained within the elastomeric sleeve through the perforations to the esophageal tissue.

In additional aspects, one or both of the first and second flexible tubes include perforations on distal portions thereof to facilitate delivery of liquids or materials.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

PRIOR ART

PRIOR ART

PRIOR ART

PRIOR ART

PRIOR ART

DETAILED DESCRIPTION

As has been described above, the techniques of this disclosure generally relate to devices and methods to reduce invasive interventions for esophageal surgery and recovery by provision of a device that removes the need for repetitive, separate pneumatic dilations for esophageal strictures and separate use of gastric invasive installation of a feeding tube and separate installation of biopsy or tissue sampling devices and separate installations of a device to administer drugs to improve healing and regeneration. Such a device advantageously provides combined esophageal stenting, pneumatic dilation, drug delivery, tissue sampling and enteral feeding aspects.

In one aspect, the present disclosure provides a first flexible tube having a distal end configured to be threaded through the nose of a patient, down the esophagus and into the stomach for enteral feeding, a second flexible tube disposed adjacent or interior to the first tube having a distal end proximate to the distal end of said first flexible tube, the distal end of said second tube configured to terminate inside the esophagus and outside of the first flexible tube for sampling, imaging or biopsying the local environment, an inflatable balloon configured around said first and second flexible tubes, the inflatable balloon disposed proximal to the distal end of the first and second flexible tubes, a third flexible tube in fluid communication with said balloon configured to inflate said inflatable balloon; and a fourth flexible tube having a distal end portion communicating with an exterior portion of said inflatable balloon, the fourth tube configured to transport suspensions or solutions of materials, such as therapeutic molecules into a space exterior to said inflatable balloon.

In another aspect, there is an elastomeric sleeve configured around both first, second and third flexible tubes, the inflatable balloon, and the fourth tube, with a length similar or equal to that of the inflatable balloon. The fourth tube communicates with an elastomeric sleeve the interior space located between the inflatable balloon and the elastomeric sleeve. The elastomeric sleeve is configured to receive and dispense therapeutic molecules to esophageal tissue outside the device. In further aspects, the elastomeric sleeve includes perforations on a surface thereof; and inflation of the inflatable balloon forces therapeutic molecules contained within the elastomeric sleeve through the perforations to the esophageal tissue.

In additional aspects, one or both of the first and second flexible tubes include perforations on distal portions thereof to facilitate delivery of liquids or materials.

In additional aspects, the elastomeric sleeve may be textured to improve stenting function.

Figure 1:
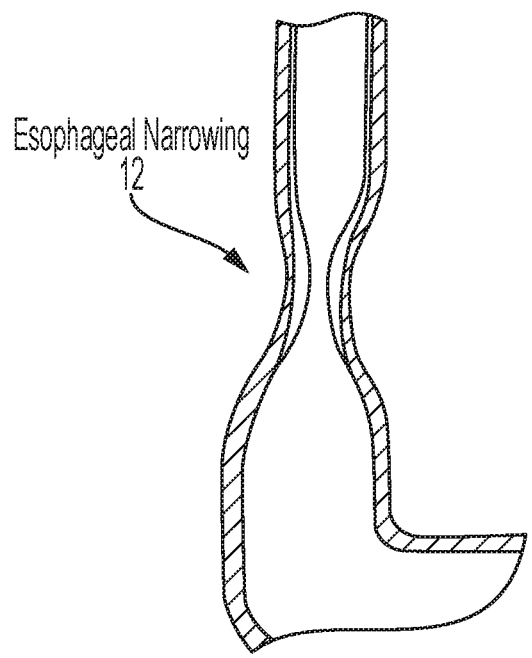
FIG. 1 is a conceptual diagram that illustrates an example of esophageal narrowing.
Figure 2:
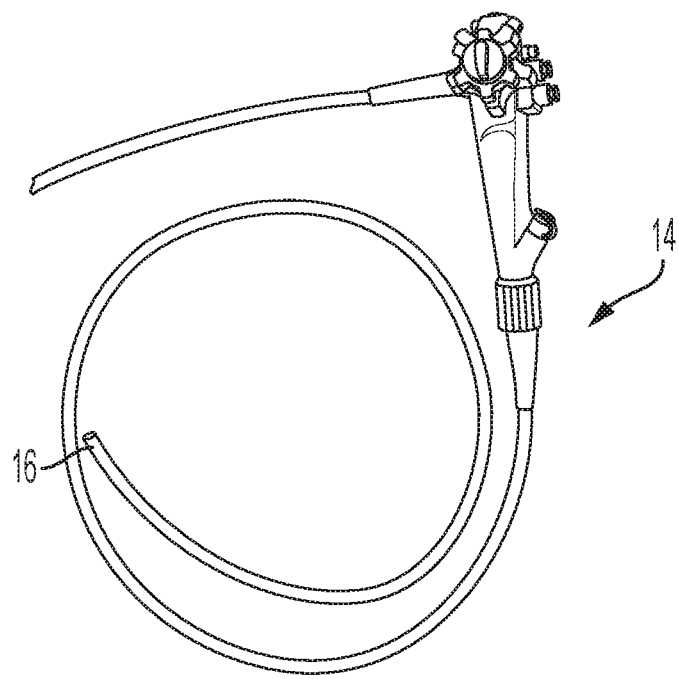
FIG. 2 is a side elevation view of an esophageal endoscope.
Figure 3:
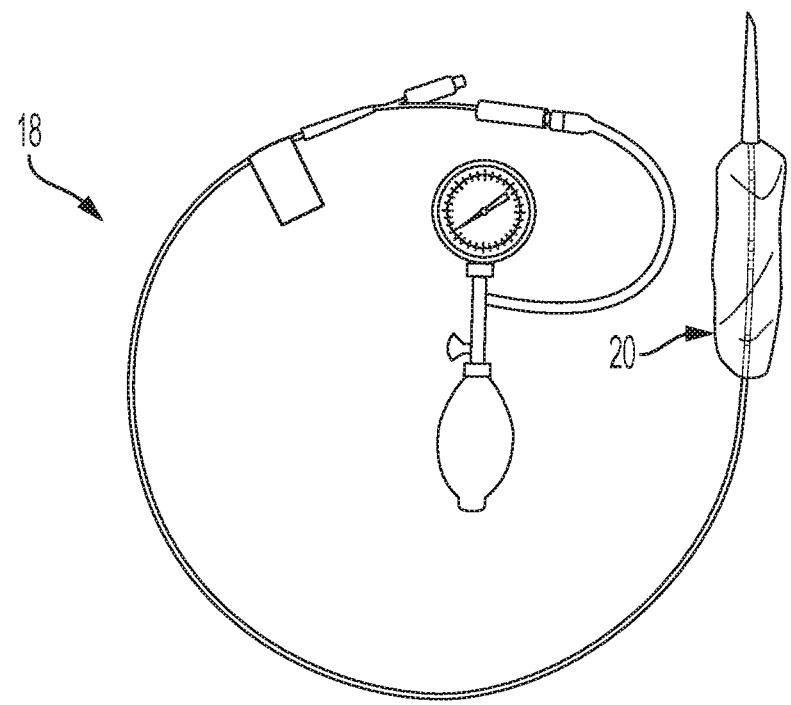
FIG. 3 is a side elevation view of a pneumatic dilator.
Figure 4:
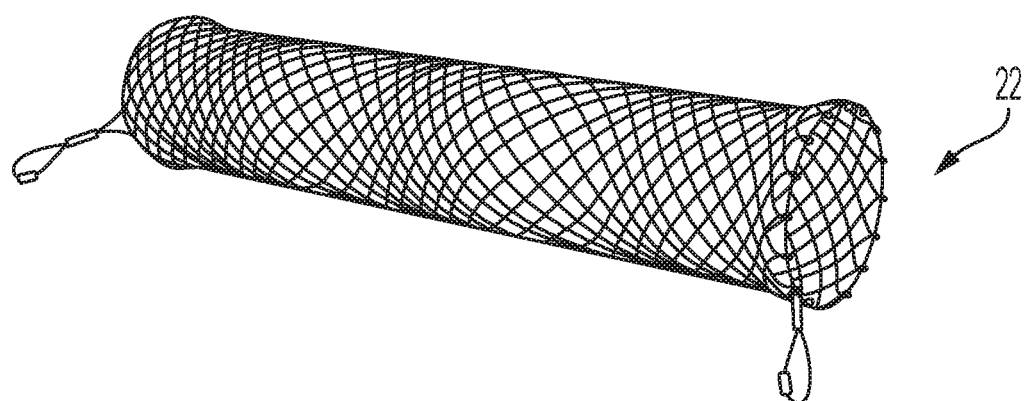
FIG. 4 is a perspective view of an esophageal stent.
Figure 5:
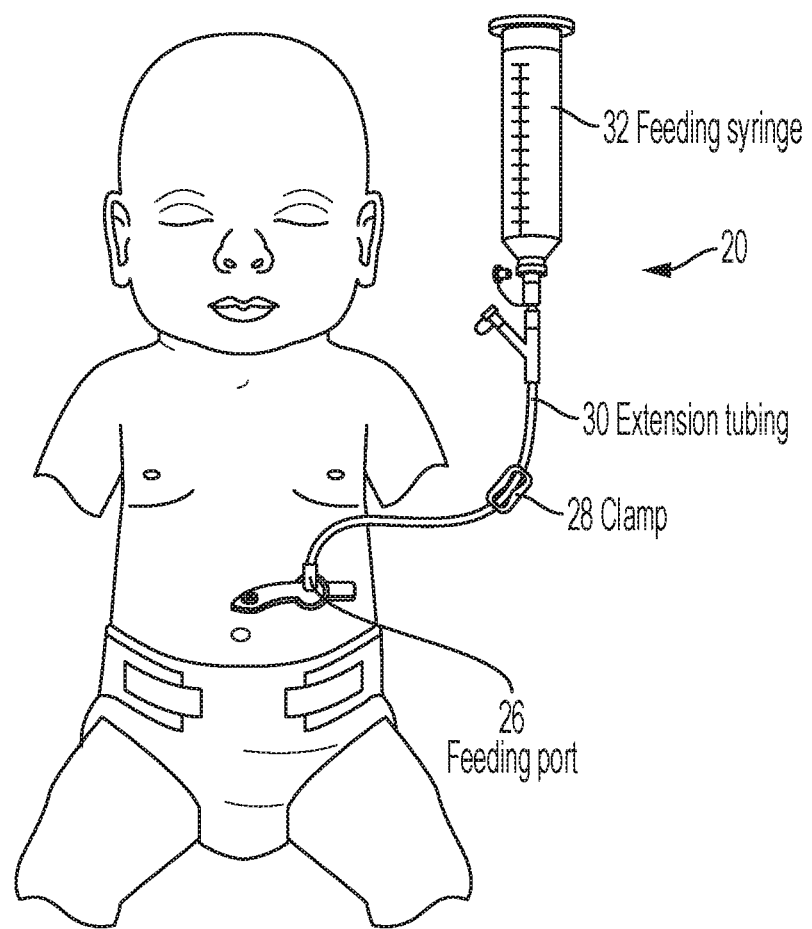
FIG. 5 is a conceptual diagram of a gastrostomy feeding tube.
Figure 6:
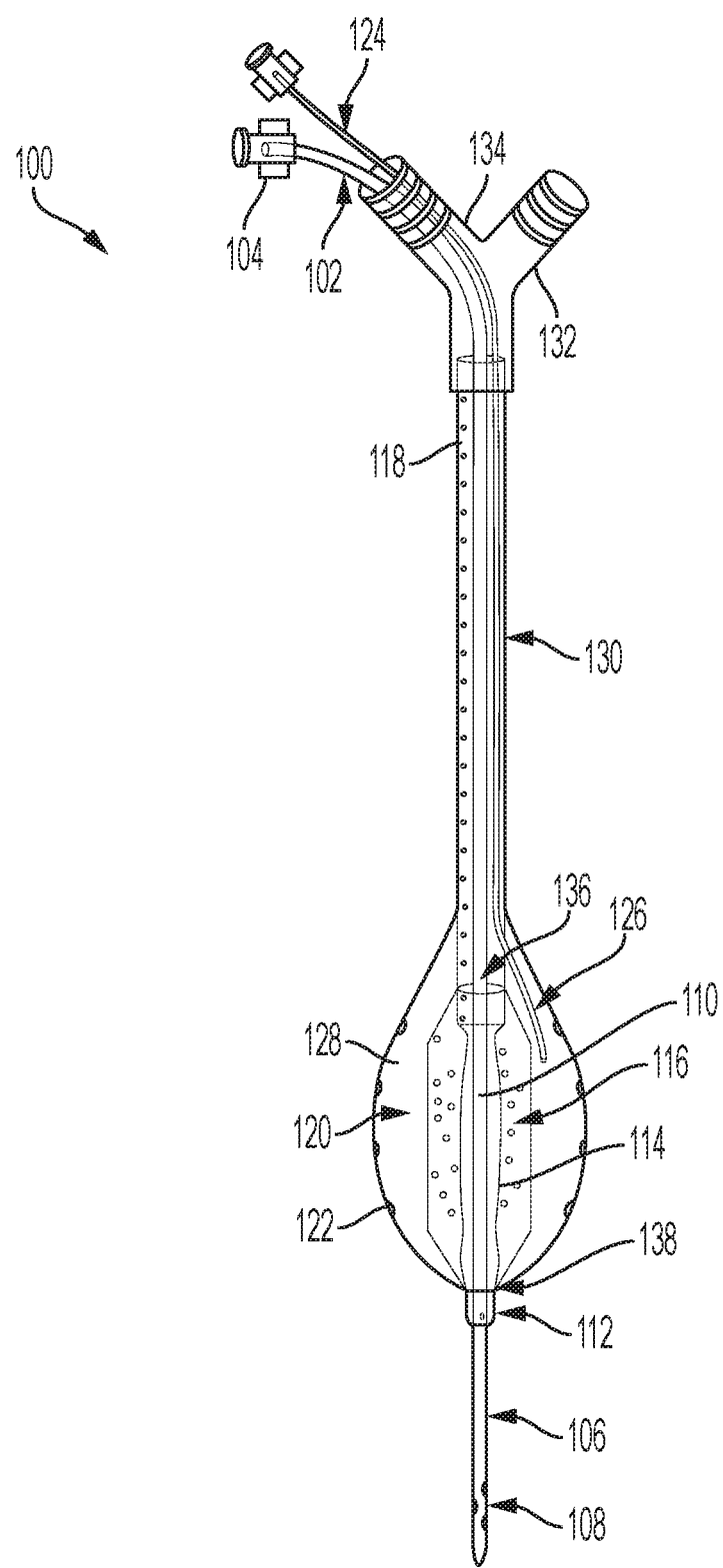
FIG. 6 is a side elevation view of an exemplary nasogastric device in accordance with the present disclosure.

Referring now to FIG. 6, an exemplary nasogastric device is illustrated generally at 100. A first flexible tube 102 is configured for enteral feeding and may include a proximal Luer port 104, a distal end portion 106, including a portion 108 having perforations thereon and an intermediate portion 110. A sampling/biopsy port is illustrated at 112, which is provided on a distal portion of a second flexible tube 114 that extends past the distal end of the inflatable balloon 116 and may be located within or adjacent to tube 102. A third flexible tube 118 provides an inflation lumen for the balloon 116 and terminates at the proximal end with a leuer port for connection to an inflation device. An elastomeric sleeve 120 is provided around the balloon 116 and includes perforations 122. Medication or other fluids provided through the fourth flexible tube 124 pass through a distal end portion 126 of the fourth flexible tube and into the volume 128 elastomeric sleeve that is exterior to the inflatable balloon and interior to the elastomeric sleeve. Inflation of the balloon 116 forces such medication or other fluids out of perforations 122 to the esophageal tissue.

Referring still to FIG. 6, in exemplary embodiments the second tube may serve as a guide for a separate flexible tube inserted into the second tube or otherwise provided parallel to the first, third and fourth flexible tubes. FIG. 6 also illustrates a junction 132, a stopper 134 and proximal and distal radiopaque balloon markers 136, 138.

Figure 7:
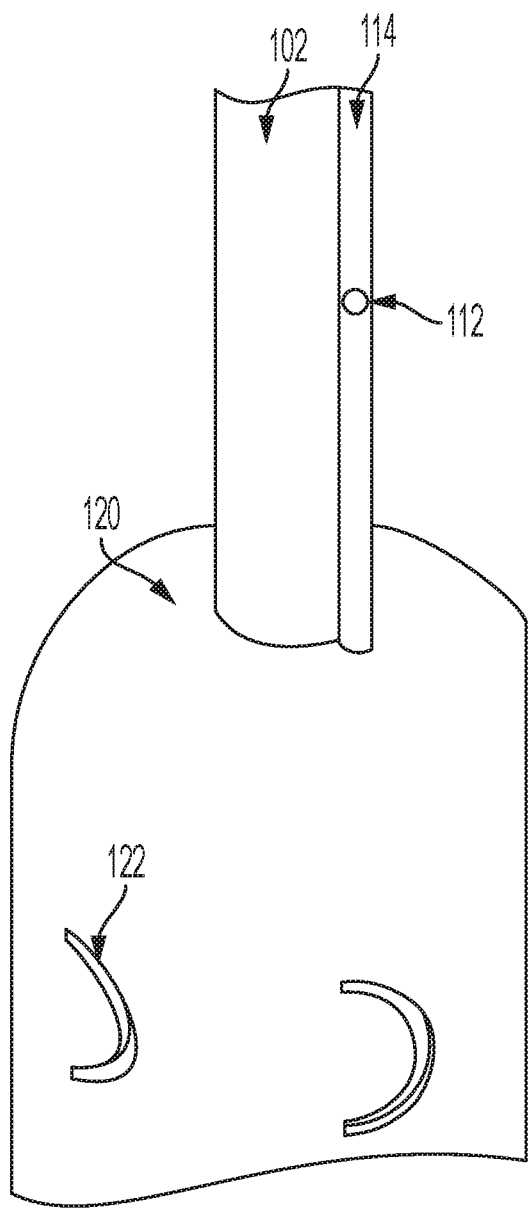
FIG. 7 is a close-up perspective view of a proximal end of the balloon portion of an exemplary nasogastric device in accordance with the present disclosure.

FIG. 7 illustrates an exemplary configuration wherein the second flexible tube 114 is provided alongside the first flexible (feeding) tube 102. As before, this second flexible tube 114 is configured for delivery of therapeutics or for sampling. In this embodiment, the second flexible tube 114 runs with the first flexible tube inside of the balloon (Note that FIG. 7 shows the elastomeric sleeve 120, which in this example surrounds the first balloon 116 (not shown). In addition to the distal sampling port 112 shown in FIG. 6, FIG. 7 shows a sampling port 112 proximal to the balloon. FIG. 7 also illustrates perforations 122 as semi-circular slits.

The illustrated exemplary balloon/elastomeric sleeve configuration provides a structure that stents the area, but that can also be dilated by using pneumatic pressure to expand the balloon. A therapeutic material, e.g., carried in a gel substrate between the balloon and elastomeric sleeve can be used for slow delivery of modulating substances through holes in the outer elastomeric sleeve when expanding the balloon to prevent stricture of the esophagus.

First flexible tube (nasogastric tube) 102 extends through the balloon and into the stomach 142. Third flexible tube 118 is in communication with the inflatable balloon 116. Second flexible tube 114 is provided with a sampling port mid-balloon for sampling of the esophageal lumen or for direct drug delivery.

Table 1, below, provides exemplary, non-limiting materials for various possible components:

TABLE 1

| Component | Material/Composition |
| --- | --- |
| Delivery Conduit | poly(vinyl chloride) (PVC), urethanes, silicone |
| Balloon | Thermoplastic or thermoplastic elastomer, for example thermoplastic PEBAX or polyethylene terephthalate (PET) |
| Elastomeric sleeve | Silicone elastomer (possibly coated with hyaluronan, hydrophilic materials, such as sodium hyaluronic salt, polyvinylprolidone (PVP) or polyurethane), polyamide elastomers, polyurethane elastomers, polyester elastomer, poly(ethylene terephthalate), poly(vinyl chloride), polyethylene, Sylgard 186, Sylgard 184, chlorinated neoprene, e.g., Chronoprene or C-Plex |
| Radio-opaque Markers | Stainless Steel Band, platinum/iridium markers |
| Tubing Connections (Luer Ports) | Polypropylene |
| Main Feeding Conduit | poly(vinyl chloride) (PVC), urethanes, silicone |
| Balloon Inflation Conduit | poly(vinyl chloride) (PVC), urethanes, silicone, polyether block amides (e.g., PEBAX), polyethyleneterephthalate (PET), polybutylene terephthalate (PBT), polyethylene naphthalate (PEN) |

In exemplary embodiments, the various flexible tubes comprise nontoxic flexible polymer material. In various portions below, the first flexible tube will also be referred to in a non-limiting way as a "feeding conduit." Further, the second flexible tube will be referred to in a non-limiting way as a "biopsy conduit." Third flexible tube will be referred to in a non-limiting way as a "balloon inflation conduit." Fourth flexible tube will be referred to in a non-limiting way as an "injectable conduit." Collectively in part or in whole, the first through fourth tubes may also be referred to as "the conduits."

The mechanical properties of the conduits can be tailored by varying one or more reactants in the material. The Young's modulus may vary from 10 Pa to 1 GPa. The sizes of many aspects of this device can be tailored to a neonatal, pediatric or adult application. In exemplary aspects, the conduits range in length from about 3 to 10 centimeters (cm). In an aspect, the radius of the feeding conduit ranges from about 2 to about 10 millimeters (mm). In another aspect, the radius of the delivery conduit ranges from about 1 millimeter to 1 centimeter.

In further aspects, the radius of the device after it is inflated is between about 10 millimeters and 30 millimeters, depending on pediatric or adult patient requirements. In additional exemplary aspects, the radius of the device when collapsed and not inflated may be between about 4 and 10 millimeters in diameter. The balloon portion of the device will remain deflated until a time is needed to deliver drugs or treat for a potential stricture. In further aspects, the radius of the deflated balloon and conduits should be less than the current diameter of the esophagus as to prevent the native esophagus from continuously touching the balloon and device.

In additional advantageous aspects, the conduits may be designed to be stable against degradation in vivo for a period of at least one year. The conduits may be sterilized using techniques appropriate for medical tubing, including autoclaving, ethylene oxide treatments, plasma treatments, and irradiation. The conduits may contain tracer molecules (radiopaque markers, near infrared dyes, fluoroscopic markers, or other agent(s)) to allow visualization of the placement of the device. As we noted above, FIG. 6 provides radiopaque markers proximal and distal to the balloon to aid in visualization during placement and otherwise.

In exemplary aspects, when the device is placed, the proximal end of the feeding conduit is located outside of the patient; and the distal end is in the stomach of the patient. In certain embodiments at least the last 5 centimeters of the distal end of the feeding conduit tubing contains perforations that may be elliptical or another shape (e.g., having a long axis of about 1-8 millimeters in length) to allow material injected into the feeding conduit to exit freely into the stomach. In other embodiments, the entire last 5 centimeters includes perforations.

In further exemplary aspects, when the device is placed, the proximal end of the biopsy conduit is located outside of the patient, and the distal end is located in the esophagus about 1-10 centimeters below the distal end of the inflatable balloon. This distal section of the biopsy conduit contains perforations that may be elliptical or another shape (e.g., having a long axis of about 1-3 millimeters in length) to assist in delivery of liquids and/or sampling of the local environment. Delivery of liquids may be achieved by attaching a syringe containing desired liquid and applying positive pressure to the port at the proximal end of the conduit, though other similar techniques are contemplated. Sampling of liquid may be achieved by attaching a syringe void of liquid and applying negative pressure ("suction") to the port at the proximal end of the conduit, though other similar techniques are contemplated.

In further exemplary aspects, when the device is placed, the proximal end of the balloon inflation conduit is located outside of the patient, and the distal end is located inside the balloon. For example, the end of the balloon inflation conduit may be placed such that it is within the proximal 25% of the balloon's length.

In further aspects, when the device is placed, the proximal end of the injectable conduit is located outside of the patient, and the distal end is located between the balloon and the elastomeric sleeve. For example, the end of the injectable conduit may be placed such that it is within the proximal 10-50% of the balloon/elastomeric sleeve's length.

In further exemplary aspects, the inflatable balloon comprises a nontoxic material with composition that may contain silicone elastomer, polyvinyl chloride, polyether block amides (e.g., PEBAX), polyethyleneterephthalate (PET), polybutylene terephthalate (PBT), polyethylene naphthalate (PEN), polyethylene, polyethylene terephthalate, or nylon. The mechanical properties of the balloon can be tailored by varying one or more reactants in the material. The Young's modulus may vary from 10 Pascals (Pa) to 1 Gigapascal (GPa). The initial radius of the balloon ranges from 5 millimeters to 2 centimeters; and this radius may reach up to 1000% its initial value when the balloon is inflated. In exemplary aspects, the initial length of the balloon may vary from about 0.5 to 30 centimeters. In certain aspects, the balloon material is designed to be stable against degradation in vivo for a period of at least one year. The balloon may be sterilized using techniques appropriate for medical tubing, including autoclaving, ethylene oxide treatments, plasma treatments, and irradiation. The balloon may contain tracer molecules (radiopaque markers, near infrared dyes, fluoroscopic markers, or other agent(s)) to allow visualization of the placement of the device.

The inflatable balloon may be inflated fully or partially by applying positive pressure to the balloon inflation conduit (118 in FIG. 6). Positive pressure may be maintained by sealing the valve at the port on the proximal end of the balloon inflation conduit, increased by applying more air to the balloon inflation conduit, or decreased by removing air from the balloon inflation conduit.

In exemplary aspects, the elastomeric sleeve that partially or completely surrounds the inflatable balloon and comprises a nontoxic elastomer film with composition that may be made of any of the materials listed for the inflation balloon. The mechanical properties of the balloon can be tailored by varying one or more reactants in the material. The Young's modulus may vary from 10 Pa to 1 GPa. In some, but not all exemplary aspects, the drug delivery elastomeric sleeve covers the entire inflation balloon, except for the perforations. When the balloon is not dilated, the elastomeric sleeve is in contact with and may or may not be permanently bonded to the balloon at the proximal and distal end of the balloon. The perforations in the outer drug delivery balloon may be grouped together for example in a hemispherical shape with dimensions that range from 0.5 micrometers to 25 mm depending on the extent of expansion of the balloon. Perforations are not connected to neighboring perforations. The perforations are designed to be closed when balloon is not dilated and to open when the balloon is inflated or during the inflation process. As we have noted, the elastomeric sleeve may be designed to be stable against degradation in vivo for a period of at least one year. The elastomeric sleeve may be sterilized using techniques appropriate for medical tubing, including autoclaving, ethylene oxide treatments, plasma treatments, and irradiation. The elastomeric sleeve may contain tracer molecules (radiopaque markers, near infrared dyes, fluoroscopic markers, or other agent(s)) to allow visualization of the placement of the device.

In further exemplary aspects, the injectable conduit (the fourth flexible tube) allows filling of the space between the inflatable balloon and the elastomeric sleeve with therapeutic molecules. In exemplary embodiments, this may comprise a viscous liquid, a shear thinning fluid, and/or a gel (herein referred to as "therapeutic vehicle"), which may contain a therapeutic agent. Loading of the injectable may be accomplished prior to device placement in patient by completely deflating balloon, applying a syringe containing the therapeutic vehicle (with or without therapeutic agent) to the port at the proximal end of the injectable conduit and injecting the desired volume.

In exemplary aspects, the elastomeric sleeve contains perforations that remain closed when the inflation balloon is completely deflated to allow filling with therapeutic vehicle (with or without therapeutic agent). Liquids, shear thinning fluids, or gels may also be injected through the injectable conduit when the device is placed to break down therapeutic vehicles, to release agents, or to refill the space with the same or new therapeutic agents. In the absence of positive pressure applied to the conduit, shearing of the vehicle, or opening of the perforations in the elastomeric sleeve, the vehicle is designed to remain in the space between the balloon and the elastomeric sleeve. Expansion of the inflation balloon is designed to push the therapeutic vehicle through the perforations in elastomeric sleeve. Inflation of the inflatable balloon causes deformation in the flexible elastomeric sleeve that surrounds the balloon. In exemplary embodiments, semi-circular slits in the flexible elastomeric sleeve will open more as the inflation balloon dilates, which permits delivery of therapeutics in a gel vehicle with increased balloon inflation.

Exemplary aspects described herein provide nurses, surgeons and gastroenterologists treating pediatric and/or adult patients who have undergone esophageal surgery due to congenital defects, caustic injuries, esophagitis, Barrett's esophageal diseases or esophageal cancer a nasogastric device an method that avoids the problems and disadvantages of the prior art, including avoiding initial plural interventional procedures requiring sedation as well as follow-up, repetitive interventional procedures similarly requiring such sedation.

In certain esophageal cases, this device can be placed immediately after resection of the esophagus following caustic ingestion or after repair of a long gap esophageal atresia in order to ensure the lumen remains patent during healing. Strictures occur due to severe inflammation that can lead to esophageal narrowing and the inability to drink or eat. Exemplary embodiments provide for effective use of the device as a stent, dilator, drug administrator and enteral feed device, without the above-described disadvantages.

In exemplary embodiments, a method of using said nasogastric device includes any of the above described uses, inclusive of, for example, positioning the nasogastric device utilizing visualized radiopaque markers at an esophageal stricture; injecting a therapeutic vehicle through said fourth flexible tube; and inflating said inflatable balloon against said esophageal stricture and simultaneously delivering said therapeutic vehicle to esophageal tissue adjacent to the device, among others.

In addition, this device can easily be adapted for use in the small intestine for strictures from Crohn's disease or intestinal cancer. In addition to surgical cases of esophageal diseases, patients suffering from other intestinal diseases such as Crohn's disease can also suffer from severe strictures, which would normally be treated with surgical resection. The length of this device can be manipulated and adapted to enable treatment of more distal strictures.

In addition this device can be adapted for use in urethral expansion of strictures.

Most importantly, disclosed aspects provide a device that decrease the number of invasive interventions required. A single tube that can deliver medication to a site of stricture, that can be intermittently used as a dilator, and that can be utilized for enteral feeding is a revolutionary advancement for patients suffering from esophageal diseases. Apart from the relatively simple reduction in cost because of reduce repetitive invasive procedures, such a device and method minimizes repeat surgeries and is particularly valuable for infants and children because of the reduction in the number of times of otherwise required surgery with sedation. Additionally, regardless of a patient's age, if a stricture were to occur, drugs could be delivered directly to the site using the separate port for drug delivery, again without the need for additional costly interventions. Further, with regard to integral enteral feeding, delivery of food does not mix with separate delivery of drugs, when required.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

While the invention has been described with reference to preferred embodiments, it will be understood by those skilled in the art that various changes may be made and equivalents may be substituted for the elements thereof without departing from the scope of the invention. In addition, many modifications may be made to adapt the teaching of the invention to particular use, application, manufacturing conditions, use conditions, composition, medium, size, and/or materials without departing from the essential scope and spirit of the invention. Therefore, it is intended that the invention not be limited to the particular embodiments and best mode contemplated for carrying out this invention as described herein.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and words of a similar nature in the context of describing the improvements disclosed herein (especially in the context of the following claims) are to be construed to cover both the singular and the plural, unless otherwise indicated herein or clearly contradicted by context. Further, it should further be noted that the terms «first," "second," and the like herein do not denote any order, quantity, or relative importance, but rather are used to distinguish one element from another. The modifier "about" used in connection with a quantity is inclusive of the stated value and has the meaning dictated by the context (e.g., it includes, at a minimum the degree of error associated with measurement of the particular quantity).

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed.

Unless defined otherwise, all technical and scientific terms used herein have the same meaning as is commonly understood by one of skill in the art to which this invention belongs.

The invention claimed is:

1. A nasogastric device, comprising: a first flexible tube having a distal end configured to be threaded through a nose of a patient, down an esophagus and into a stomach; a second flexible tube disposed adjacent to the first tube having a distal end proximate to the distal end of said first flexible tube, the distal end of said second tube configured to terminate inside the esophagus; an inflatable balloon configured around said first and second flexible tubes, the inflatable balloon disposed proximal to the distal end of the first and second flexible tubes; a third flexible tube in fluid communication with said inflatable balloon configured to inflate said inflatable balloon; and a fourth flexible tube having a distal end portion communicating with an exterior portion of said inflatable balloon, the fourth tube configured to transport suspensions or solutions of materials, such as therapeutic molecules into a space exterior to said inflatable balloon and an elastomeric sleeve at least partially surrounding said inflatable balloon, the elastomeric sleeve in fluid communication with said fourth tube, the elastomeric sleeve including perforations configured to allow release of said therapeutic molecules there through.

2. A nasogastric device in accordance with claim 1, wherein at least a last 5 centimeters of the distal end of said first flexible tube includes perforations.

3. A nasogastric device in accordance with claim 1, wherein said inflatable balloon has an initial radius of between about 5 millimeters and 2 centimeters.

4. A nasogastric device in accordance with claim 1, wherein said inflatable balloon has an initial length of between about 0.5 and 30 centimeters.

5. A nasogastric device in accordance with claim 1, wherein the elastomeric sleeve is configured to closely surround at least a portion of the inflatable balloon such that inflation of the inflatable balloon pushes the therapeutic molecules contained within the elastomeric sleeve through the perforations of elastomeric sleeve.

6. A nasogastric device in accordance with claim 1, further comprising at least one radiopaque marker provided near a distal portion of an element of said nasogastric device.

7. A nasogastric device in accordance with claim 1, further comprising ports configured at the proximal ends of each of said first, second third and fourth flexible tubes.

8. A nasogastric device in accordance with claim 1, wherein the distal end of said second flexible tube extends between 1 and 10 centimeters below the distal end of said inflatable balloon.

9. A nasogastric device in accordance with claim 8, wherein at least a portion of said distal end of the second flexible tube includes perforations that have a length of between 1 and 3 millimeters.

10. A nasogastric device in accordance with claim 1, wherein at least a portion of the distal end of said first flexible tube includes perforations configured to allow said therapeutic molecules to exit freely into the stomach.

11. A nasogastric device in accordance with claim 10, wherein said perforations of the distal end of said first flexible tube have a length between 1 and 8 millimeters.

12. A nasogastric device in accordance with claim 10, wherein said perforations of the elastomeric sleeve are configured as semicircular patterns.

13. A nasogastric device in accordance with claim 12, wherein said perforations of the elastomeric sleeve have lengths between about 0.5 micrometers and 25 millimeters.

14. A method of treating an esophageal stricture, comprising: providing a nasogastric device, including: a first flexible tube having a distal end configured to be threaded through a nose of a patient, down an esophagus and into a stomach; a second flexible tube disposed adjacent to the first tube having a distal end proximate to the distal end of said first flexible tube, the distal end of said second tube configured to terminate inside the esophagus; an inflatable balloon configured around said first and second flexible tubes, the inflatable balloon disposed proximal to the distal end of the first and second flexible tubes; a third flexible tube in fluid communication with said inflatable balloon configured to inflate said inflatable balloon; and a fourth flexible tube having a distal end portion communicating with an exterior portion of said inflatable balloon, the fourth tube configured to transport suspensions or solutions of materials, such as therapeutic molecules into a space exterior to first inflatable balloon; and positioning said nasogastric device utilizing visualized radiopaque markers at an esophageal stricture; injecting said therapeutic molecules through said fourth flexible tube; and inflating the inflatable balloon against said esophageal stricture and simultaneously delivering said therapeutic molecules to esophageal tissue adjacent the inflatable balloon; wherein an elastomeric sleeve at least partially surrounds said inflatable balloon, and wherein said inflating of said inflatable balloon forces said therapeutic molecules through perforations of elastomeric sleeve to esophageal tissue adjacent to the device.

15. A method in accordance with claim 14, wherein the distal end of said second flexible tube extends between 1 and 10 centimeters below the distal end of said inflatable balloon.

16. A method in accordance with claim 15, wherein at least a portion of said distal end of the second flexible tube includes perforations that have a length of between 1 and 3 millimeters.

17. A method in accordance with claim 14, further comprising additionally providing enteral feeding via said first flexible tube.

18. A method in accordance with claim 17, wherein said first flexible tube includes perforations on at least a distal portion thereof to facilitate said enteral feeding.

19. A method in accordance with claim 17, wherein said perforations have a length of between 1 and 8 millimeters.

* * * * *